United States Patent [19]

Hunold

[11] Patent Number: 4,875,225

[45] Date of Patent: Oct. 17, 1989

[54] X-RAY VIDEO SYSTEM AND METHOD FOR THE TRANSILLUMINATION OF AN EXAMINATION SUBJECT

[75] Inventor: Michael Hunold, Ottweiler, Fed. Rep. of Germany

[73] Assignee: Siemens Aktiengesellschaft, Berlin and Munich, Fed. Rep. of Germany

[21] Appl. No.: 150,846

[22] Filed: Feb. 1, 1988

[30] Foreign Application Priority Data

Feb. 16, 1987 [DE] Fed. Rep. of Germany ....... 3704859

[51] Int. Cl.$^4$ .............................................. A61B 6/06
[52] U.S. Cl. .................................... 378/99; 378/147; 378/162
[58] Field of Search .......... 378/99, 147, 148, 149–152, 378/205, 204, 207, 162–164; 358/111

[56] References Cited

U.S. PATENT DOCUMENTS

| | | |
|---|---|---|
| 3,668,402 | 6/1972 | Palermo et al. |
| 3,934,151 | 1/1976 | Stowe et al. |
| 4,174,481 | 11/1979 | Liebetruth ............................ 378/99 |
| 4,514,859 | 4/1985 | Holzer . |
| 4,609,940 | 9/1986 | Born et al. |
| 4,672,652 | 6/1987 | Huttenrauch et al. |
| 4,730,351 | 5/1988 | Heumann ............................. 378/99 |

FOREIGN PATENT DOCUMENTS

| | | |
|---|---|---|
| 0176282 | 4/1986 | European Pat. Off. |
| 2053089 | 2/1980 | Fed. Rep. of Germany . |
| 3030332 | 2/1982 | Fed. Rep. of Germany . |
| 3147128 | 6/1983 | Fed. Rep. of Germany . |
| 3436866 | 4/1986 | Fed. Rep. of Germany . |
| 8436281 | 5/1986 | Fed. Rep. of Germany . |
| 2393496 | 2/1979 | France ................................ 378/99 |
| 0085687 | 5/1983 | Japan ................................ 358/111 |

Primary Examiner—Carolyn E. Fields
Assistant Examiner—Joseph A. Hynds
Attorney, Agent, or Firm—Hill, Van Santen, Steadman & Simpson

[57] ABSTRACT

An x-ray video system for the transillumination of an examination subject has an x-ray system which generates a transillumination image of a patient using an x-ray beam having a central ray, a diaphragm for gating the x-ray beam which has a number of plates, each moveable relative to the central ray, a signal generator associated with each plate which generates a signal corresponding to the position of the associated plate relative to the central ray, a mixer for combining the plate position signals with the transillumination image, and a display which generates the transillumination image with the position signals mixed therewith in the form of marks on the transillumination image.

13 Claims, 4 Drawing Sheets

X-RAY VIDEO SYSTEM AND METHOD FOR THE TRANSILLUMINATION OF AN EXAMINATION SUBJECT

BACKGROUND OF THE INVENTION

1. Field of the Invention

The present invention is directed to an x-ray video system, and a method for operating such a system, for the transillumination of an examination subject wherein a video image corresponding to an x-ray image of a patient is generated on a display device, and wherein the x-ray beam used to generate the transillumination image is gated by a primary radiation diaphragm having a plurality of moveable diaphragm plates.

2. Description of the Prior Art

An x-ray video system is described in the periodical "Roentgenpraxis," 6/1981, pages 234-246 wherein an x-ray tube is used to generate an x-ray beam which is limited by a primary radiation diaphragm having a plurality of adjustable diaphragm plates. The x-ray beam is incident on a patient, and the resulting x-ray image is supplied via an x-ray image intensifier to a video chain with a video display. An image memory and image processing means are provided between the video camera, which is connected to the image intensifier, and the display. In this known system, if only a particular organ or region of a patient is of interest, the diaphragm plates of the primary radiation diaphragm are adjusted so that the x-ray beam is gated to transirradiate only the area of interest. The diaphragm plates generate shadows on the transillumination image, which are visible on the display, and are used to bring the diaphragm plates to the required position. This procedure can take a considerable time under certain circumstances, so that the patient may risk exposure to a radiation dose which is not negligible in comparison to the radiation dose required for the actual examination.

SUMMARY OF THE INVENTION

It is an object of the present invention to provide an x-ray video system of the type described above wherein the plates of the primary diaphragm can be adjusted to the desired position without subjecting the patient to a significant radiation dose beyond that required to conduct the actual examination.

The above object is achieved in accordance with the principles of the present invention in a method and apparatus wherein a path signal generator is allocated to each diaphragm plate of the primary diaphragm. The path signal generator for each plate generates a signal corresponding to the position of the associated diaphragm plate relative to the central ray of the x-ray beam. This signal is supplied to an image processor. Upon the display of a transillumination image obtained from the image memory, the image processor mixes a mark corresponding to the position of each diaphragm plate into the transillumination image. To gate a region of interest of the patient, it is thus sufficient to briefly transilluminate the patient with a completely open primary radiation diaphragm, to store the corresponding transillumination image in the image memory, and to portray the image on the display using the image processor. Gating of the organ can then be undertaken using the stored transillumination image, into which the marks corresponding to the position of the diaphragm plates have been mixed. As the positions of the plates are adjusted, the marks move on the displayed image, and the patient is not subjected to any further radiation load.

If all of the diaphragm plates of the primary radiation diaphragm are synchronously adjustable relative to each other such as, for example, in an iris diaphragm, it is sufficient to use a path signal generator allocated to a single diaphragm plate. The marks indicating the positions of the remaining diaphragm plates can be additionally mixed into the stored transillumination image with image processing means readily constructable by those skilled in the art, or with an additional computation means, also well within the knowledge of those skilled in the art, operating in combination with the image processor.

If all of the diaphragm plates of the primary radiation diaphragm are adjustable independently of each other, it is necessary to provide a path signal generator for each diaphragm plate. Primary diaphragms are also known wherein the diaphragm plates are synchronously adjustable in pairs, such as known rectangular diaphragms. For primary diaphragms of this type, it is sufficient to allocate a path signal generator to one plate in each pair, and the image processing means (or computational means) generates the mark corresponding to the other diaphragm plate of the pair.

To provide a more precise visual impression for the operator undertaking the gating of a particular region of a patient, in a further embodiment of the invention the mark which is generated is in the form of a line having a contour corresponding to the shape of the radiation-limiting edge of the associated diaphragm plate.

The path signal generator may be directly connected to the corresponding diaphragm plate. If the diaphragm plates are motor-driven, however, the path signal generator may be coupled to the motor which adjusts the position of the corresponding diaphragm plate. If the motor used to adjust the diaphragm plate is a stepping motor, the stepping motor itself may form the path signal generator, with the path signal being the control signal for the stepping motor.

DESCRIPTION OF THE PREFERRED EMBODIMENTS

Figure 1:
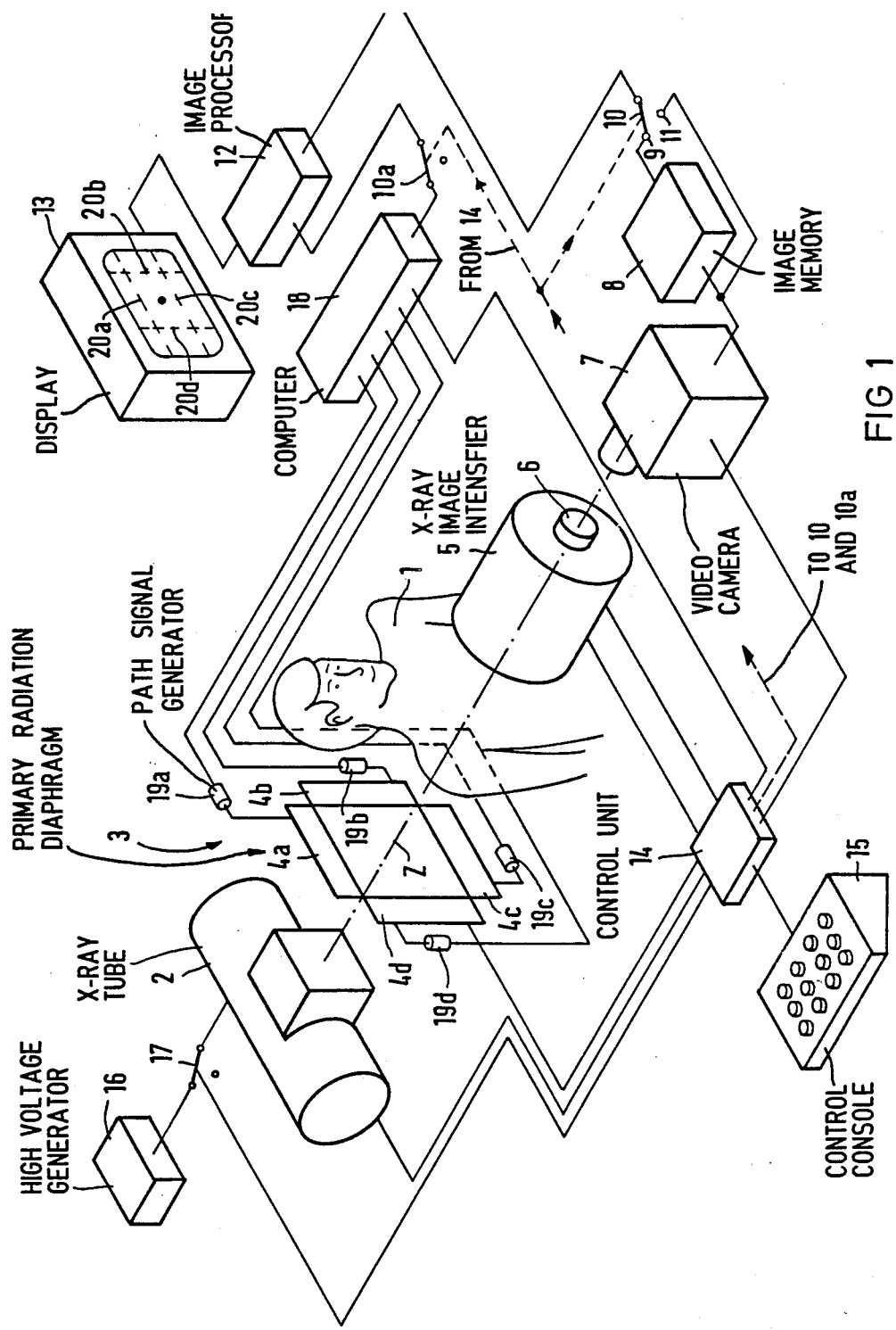
FIG. 1 is a schematic perspective view of an x-ray system, including a video system, constructed and operating in accordance with the principles of the present invention.

A x-ray examination system constructed in accordance with the principles of the present invention is shown in FIG. 1. The system is used to obtain a transillumination image of a patient 1. The system includes an x-ray tube 1 which generates a cone-shaped x-ray beam, only the central ray Z of which is shown in the drawing. The cone-shaped beam is gated with a primary radiation diaphragm 3 having diaphragm plates 4a, 4b, 4c and 4d adjustable relative to each other. The radiation is attenuated by the patient 1, and is incident on the input luminescent screen of an x-ray image intensifier 5. The intensifier 5 has an output luminescent screen 6, which supplies an image to a video camera 7. The signals from the video camera 7 are supplied to an image memory 8. The output of the image memory 8 is supplied to one pole of a switch 10. The other pole 11 of the switch 10 is connected directly to the output of the video camera 7. By means of the switch 10, a video signal from the image memory 8 or directly from the video camera 7 can be selectively supplied to an image processor 12. The image processor 12 edits the video signal for portrayal on a display 13. A control unit 14, connected to a control console 15, is provided for, among other things, causing the image memory 8 to store a transillumination image supplied thereto by the video camera 7. The control console 15, via the control unit 14, may also switch the switch 10 so that either the transillumination image from the image memory 8 or the transillumination image obtained directly from the video camera 7 is displayed on the display 13.

The control console 15, via the control unit 14, can also selectively energize and de-energize the x-ray tube. This is accomplished by opening a switch 17, connected between a high voltage generator 16 and the x-ray tube 2, whenever a transillumination image obtained from the image memory 8 is displayed on the display 13 via the switch 10.

The control console 15, via the control means 14, also permit the distance between the x-ray tube 2 and the input luminescent screen of the image intensifier 5, and the distance of the input luminescent screen from the patient 1 to be varied, as schematically indicated by the lines proceeding between the control unit 14 and each of the x-ray tube 2 and the image intensifier 5. Conventional units in the image intensifier 5 and the x-ray tube 2 provide an answerback of the current position of those components to the control unit 14.

The image intensifier 5 includes electron optics having a switchable magnification factor which can be adjusted by the control console 15 through the control unit 14, again with an answerback identifying the current magnification factor f the optics. This is schematically indicated by an additional line between the image intensifier 5 and the control unit 14.

The magnification factor of the optics of the video camera 17 can also be adjusted by the control console 15 through the control unit 14, again schematically indicated by a line between the control unit 14 and the video camera 7. An answerback identifying the current magnification factor also is provided.

Using the values for the current position of the x-ray tube 2 and the image intensifier 5 relative to the patient 1, as well as the values for the current magnification factors of the image intensifier 5 and the video camera 7, the control unit 14 generates a signal corresponding to the imaging scale of the transillumination image portrayed on the display 15, and forwards this signal to a computer 18. Each diaphragm plate has a respective path signal generator 19a, 19b, 19c or 19d allocated thereto, which generate a signal corresponding to the position of the associated diaphragm plate 4a through 4d relative to the central ray Z of the x-ray beam. These signals are also supplied to the computer 18. Taking the signal for the imaging scale obtained from the control unit 14 into consideration, the computer 18 calculates the position of the diaphragm plates 4a through 4d in the transillumination image appearing on the viewing means 13. This position is determined based on the signals supplied from the path signal generators; 9a through 9d. As soon as a transillumination image from the image memory 8 is shown on the display 13, signals corresponding to the respective positions of the diaphragm plates 4a through 4d are supplied to the display 13 through a switch 10a, coupled to the switch 10, and through the image processor 12. The image processor 12 uses the signals from the computer 18 to generate marks 20a through 20d corresponding to the respective positions of the diaphragm plates 4a through 4d, which are mixed into the transillumination image from the image memory 8. When, during portrayal of a transillumination image on the display 13 the diaphragm plates 4a through 4d are adjusted, the signals from the path signal generators 19a through 19d are modified and, via the computer 18 and the image processor 12, the corresponding marks 20a through 20d move on the displayed image on the display 13. As indicated in the drawing, the marks 20a through 20d may be lines having a contour corresponding to the radiation-limiting edges of the respective diaphragm plates.

If an organ or a region of interest of the patient 1 is to be gated with the video system as described above, the patient is first positioned relative to the central ray Z of the x-ray beam without the x-ray tube 2 being energized. This can be undertaken, as is known, using a light beam simulating the central ray Z. Subsequently, the patient 1 is briefly transilluminated with the x-ray tube 2 being energized and the corresponding transillumination image is stored in the image memory 8, and is portrayed on the display 13 through the image processor 12. The x-ray tube 2 is energized only for a period of time sufficient to obtain such an image, and is then de-energized. The diaphragm plates 4a through 4d, whose respective positions relative to the central ray A are indicated on the display 13 with the marks 20a through 20d, are then adjusted relative to each other until the organ or region to be examined is gated in the desired fashion. This procedure can be monitored at all times on the display 13. After gating of the organ or region to be examined has been completed, the actual examination is undertaken. The x-ray tube 2 is energized by appropriate actuation of the control console 15, and the switch 10 is brought to pole 11 so that the transillumination image from the video camera 7 is immediately directly displayed on the display 13 through the image processor 12. The switch 10a is at the same time switched so that mixing of the marks 20a through 20d into the transillumination image does not occur, since the shadows of the diaphragm plates 4a and 4d will be visible on the display 13.

The method and apparatus described above permit gating of an organ or a small region of a patient to be achieved with substantially no radiation load on the patient.

The computer 18 can be eliminated if the imaging scale of the x-ray video system is essentially fixed, although this may leave fluctuations or blurring caused by movement of the organ under examination inside the patient. The signals from the path signal generators 19a through 19d can be directly supplied to the image processor 12. It is also possible to combine the computer 18 and the image processor 12 into a single unit, or to make those components part of the control unit 14.

Figure 2:
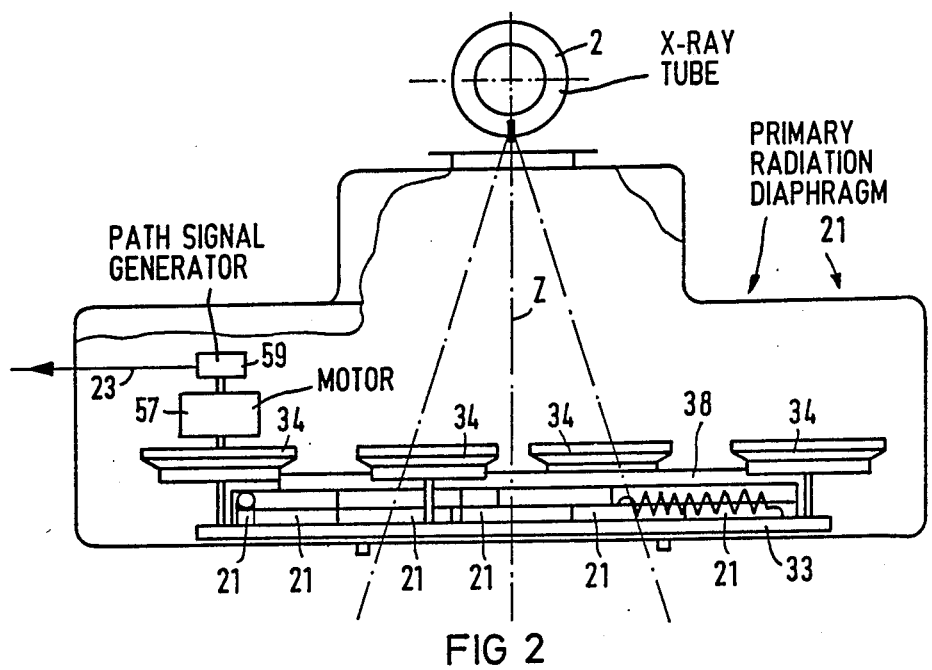
FIG. 2 is a plane view of one embodiment of a primary radiation diaphragm constructed and operating in accordance with the principles of the present invention.
Figure 3:
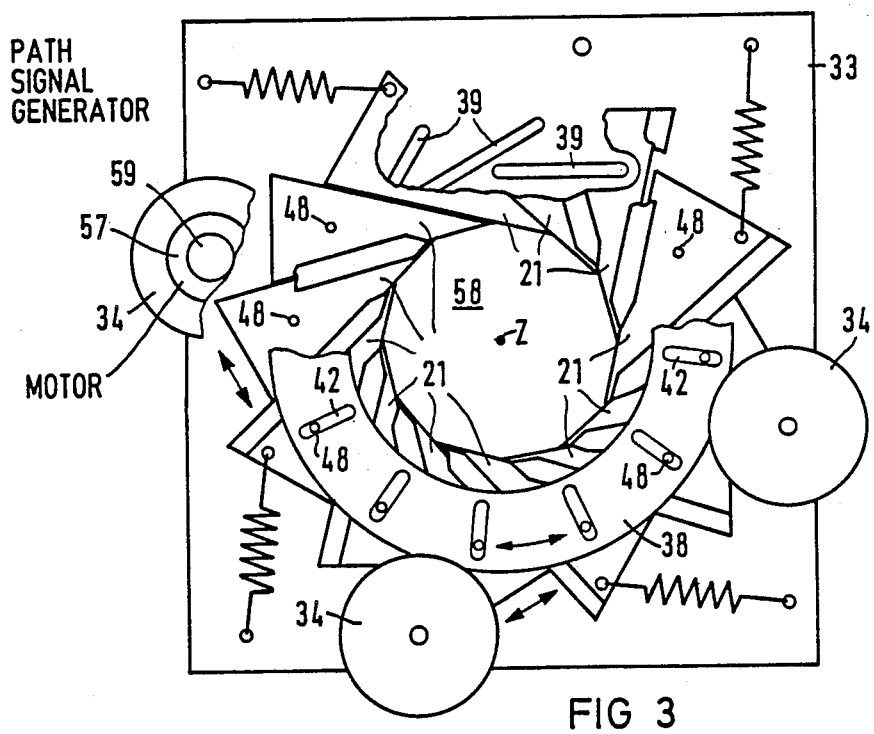
FIG. 3 is front view of the embodiment of FIG. 2.

FIGS. 2 and 3 show a first embodiment of a primary radiation diaphragm 21 including the principles of the present invention. For gating an x-ray beam having a substantially circular cross-section, the primary radiation diaphragm 21 has a plurality of triangular diaphragm plates 22, held between a carrier plate 33 and a set collar 38. The set collar 38 is rotatably seated for movement around the central ray Z of the x-ray beam by guide rollers 34. Tangential guide channels 39 are provided in the carrier plate 33, and the set collar 38 has radial guide channels 42. Each diaphragm plate 22 has a pin 48 extending into the respective channels 39 and 42. One of the guide rollers 34 is connected to a motor 57, so that the set collar 38 is rotated by the driven guide roller 34 when the motor 57 is actuated. Because each of the diaphragm plates 22 independently has its pin 48 engaging a guide channel 42 and a guide channel 39, those guide channels being perpendicularly disposed, the plates 22 will be synchronously displaced relative to the carrier plate 33 in a direction tangent to the central diaphragm aperture 58 as the set collar 38 is rotated by the motor 57. When the set collar 38 is rotated toward the left, the diaphragm aperture 58 is reduced; the aperture 58 is increased when the set collar 38 is rotated toward the right.

A path signal generator 59 is connected to the motor 57 which generates a signal corresponding to the position of the diaphragm plates 22 relative to the central ray Z. This signal is used as described above for generating a mark which is mixed into the transillumination image identifying the positions of the diaphragm plates 22 in the displayed image. This is schematically indicated in FIG. 2 by line 23, which leads to the image processor (not shown in FIG. 2). Because all of the diaphragm plates 22 are synchronously adjustable relative to each other, a single path generator 59 is sufficient, with the image processor being constructed so as to generate a plurality of marks corresponding in number to the number of plates 22, the relative positions of which are all known.

Figure 5:
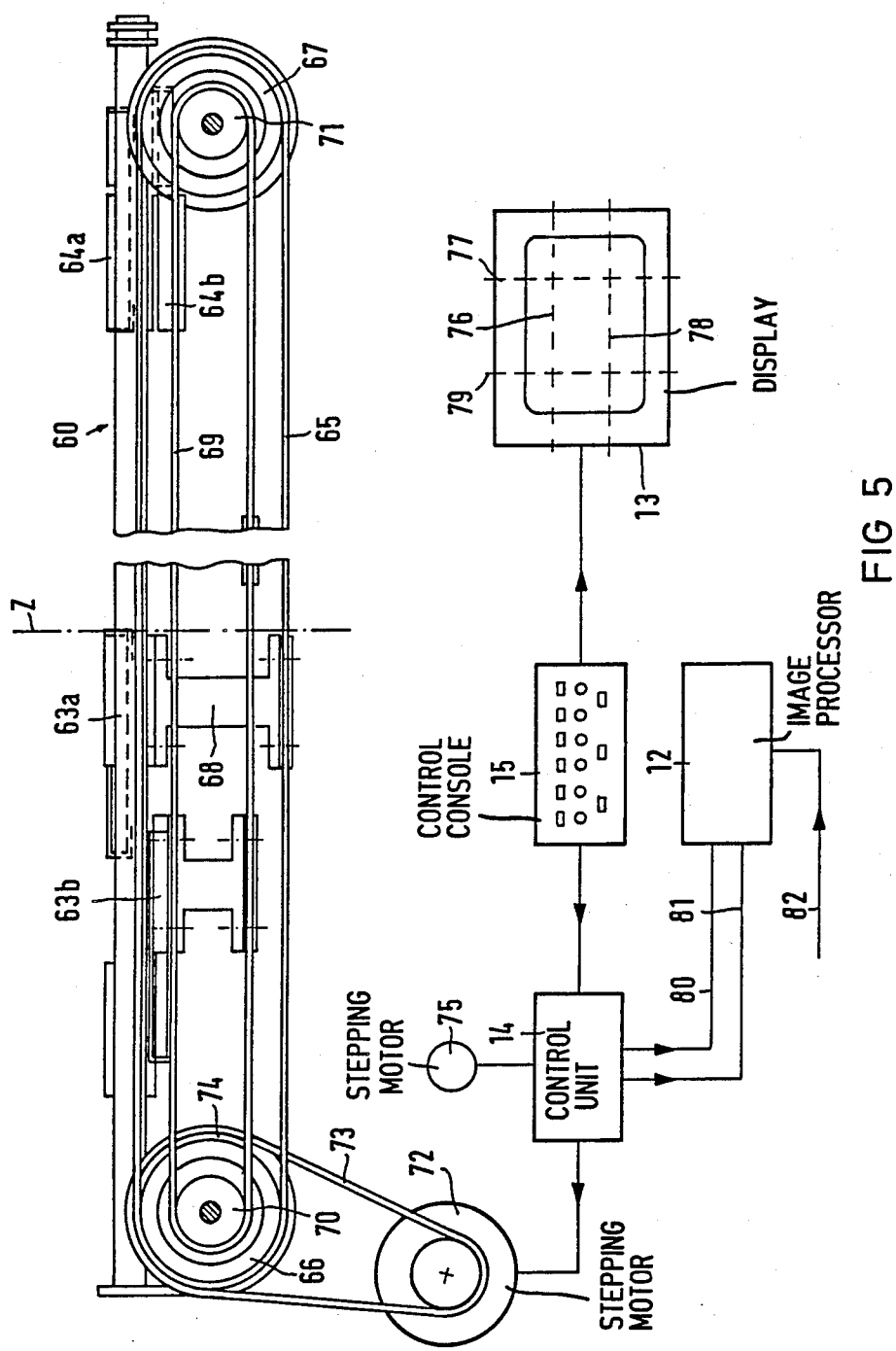
FIG. 5 is a side view, with selected components schematically shown, of the second embodiment of the primary radiation diaphragm shown in FIG. 4.

Another embodiment of a primary radiation diaphragm 60 constructed in accordance with the principles of the present invention is shown in FIG. 5. This embodiment has a rectangular diaphragm aperture 60a for gating a rectangular beam by means of eight diaphragm plates 61a, 61b, 62a, 62b, 63a, 63b, 64a and 64b (plates 64a and 64b shown only in FIG. 5).

The diaphragm plates 61a and 62a, and plates 63a and 64a are respectively synchronously adjustable in pairs relative to each other, with their edges facing toward the central ray Z limiting the diaphragm aperture 60a. The diaphragm plates 61b and 62b, and the plates 63b and 64b, follow the movement of the plates 61a and 62a (or plates 63a and 64a) so that the plates will always overlap. X-radiation passing the edges of these plates facing away from the central ray Z is blocked.

The mechanism for moving the plates 61a through 64b is shown by way of example in FIG. 5 for plates 63 through 64b. The diaphragm plates 63a and 64a are secured to a toothed belt 65, which is conducted around wheels 66 and 67. The diaphragm plate 63a is connected to the lower portion of the toothed belt 65 by a connector 68, so that the plates 63a and 64a move synchronously in opposite directions relative to each other. The diaphragm plate 64a is directly connected to the upper portion of the tooth belt 65. The diaphragm plates 63b and 64b are attached in an analogous manner to a second toothed belt 69, conducted around wheels 70 and 71. The wheels 66 and 70 are mounted for co-rotation around a common shaft, as are the wheels 67 and 71. Because the wheels 70 and 71 have a smaller diameter, the diaphragm plates 63b and 64b traverse a shorter path given rotation of the wheels through a defined angle than do the diaphragm plates 63a and 64a. The diameter of the wheels 66 and 67 is larger than the diameter of the wheels 70 and 71 by an amount such that the range of adjustment of the diaphragm plates 63a and 64a is so much larger than the range of adjustment of the diaphragm plates 63b and 64b that the pairs of plates will overlap at every diaphragm position.

For illustrative purposes only, the primary radiation diaphragm 60 is shown in a completely closed position in the left side of FIG. 5, and in a completely opened position in the right side of FIG. 5.

Adjustment of the diaphragm plates 63a through 64b is undertaken with a stepping motor 72 which, via a toothed belt 73, drives a wheel 74 seated on a common shaft with the wheels 66 and 70.

A corresponding mechanism is provided for adjustment of the diaphragm plates 61a through 62b, with only the stepping motor 75 for the drive of these diaphragm plates being schematically shown in FIG. 5. The stepping motors 72 and 75 are connected to the control unit 14 and can be activated to set a desired diaphragm aperture 60a by the control console 15.

Figure 4:
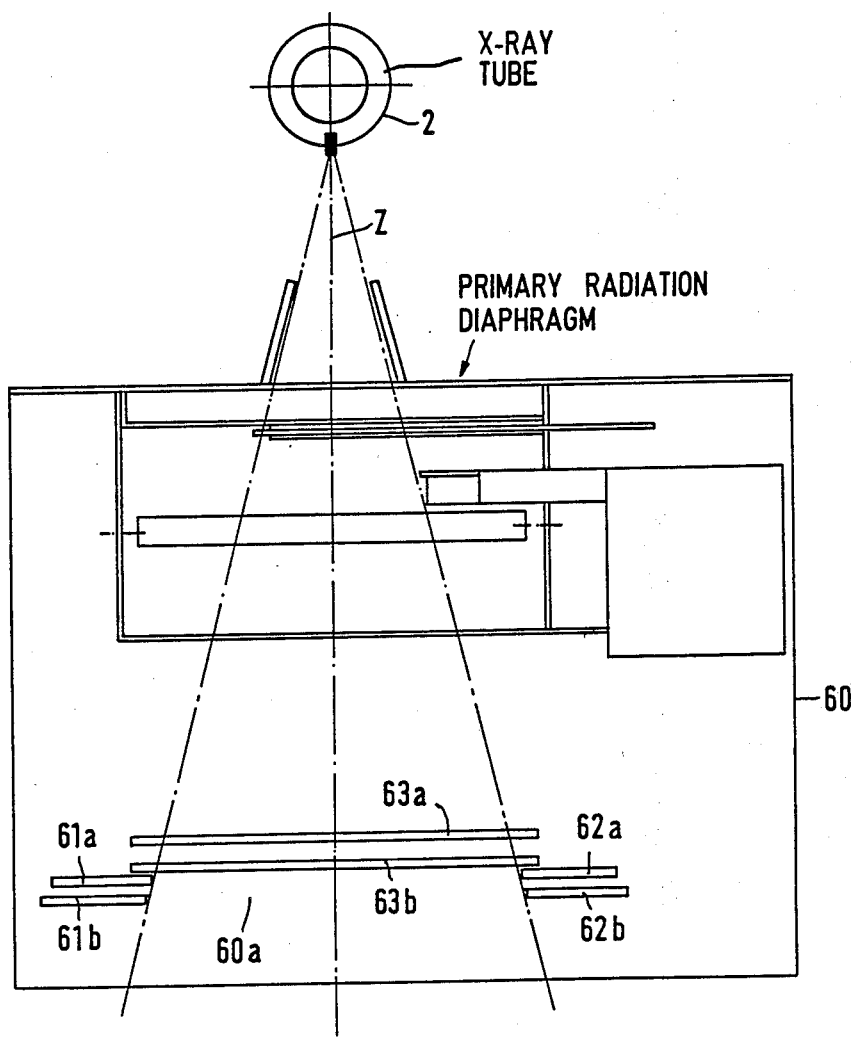
FIG. 4 is a plane view of a second embodiment of a primary radiation diaphragm constructed and operating in accordance with the principles of the present invention.

To gate an organ or a region of a patient with the embodiments of FIGS. 4 and 5, the control signals for the stepping motors 72 and 75, which correspond to their respective current rotational angles and thus to the position of the plates adjusted thereby relative to the central ray Z, are supplied additionally from the control unit 14 via lines 80 and 81 to the image processor 12. The image processor 12 mixes corresponding marks 76, 77, 78 and 79 into a transillumination image supplied via the line 82 from the image memory (not shown), and portrayed on the display 13.

In the embodiments of FIGS. 4 and 5, the path signal generators are thus formed by the stepping motors 72 and 75, and the plate position signals, used to generate the marks 76 through 79, are formed by the control signals for the stepping motors 72 and 75. Since the plates in the embodiment of FIGS. 4 and 5 are adjustable in pairs, only one path signal generator is needed for each pair of diaphragm plates. Thus no path signal generators other than the stepping motors 72 and 75 are required. The image processor 12 can compute the respective positions of each of the plates controlled by the motors 72 and 75, since it "knows" that the plates will move synchronously relative to each other. Each path signal, therefore, causes the generation of two marks (such as marks 76 and 78 or marks 77 and 79) which are mixed into the transillumination image.

The computer 18 may be either a digital computer or an analog computer.

The path signal generators 19a through 19d and 59 in the embodiments of FIG. 1 and FIGS. 2 and 3 may be potentiometers, or may be inductive, capacitative or optical signal generators as are known in the art.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray diagnostic system for examining a patient comprising:

means for generating a transillumination image of said patient using an x-ray beam having a central ray;

means for storing said transillumination image;

diaphragm means for gating said x-ray beam having a plurality of diaphragm plates each moveable relative to said central ray;

means for generating a signal corresponding to the position of a diaphragm plate in said plurality of diaphragm plates relative to said central ray;

means for visually displaying the stored transillumination image; and means for generating a mark corresponding to the said diaphragm plate from said signal and for mixing said mark into said stored transillumination image at a location in said stored transillumination image corresponding to the position of said diaphragm plate for simultaneous visual display with said stored transillumination image on said means for displaying.

2. An x-ray diagnostic system as claimed in claim 1, wherein said means for generating said signal is a means for generating a plurality of signals corresponding in number to said plurality of diaphragm plates, and includes a plurality of path signal generators respectively associated with each of said diaphragm plates.

3. An x-ray diagnostic system as claimed in claim 1, wherein said diaphragm means is a diaphragm means having at least two diaphragm plates synchronously moveable relative to each other and to said central ray, wherein said means for generating said signal includes means for generating a single signal identifying the position of all of said at least two diaphragm plates, and wherein said means for generating a mark is a means for generating respective marks corresponding to the position of each of said at least two diaphragm plates from said single signal.

4. An x-ray diagnostic system as claimed in claim 3, wherein said diaphragm means is a rectangular diaphragm means having opposite pairs of diaphragm plates with each pair of diaphragm plates forming a set of said at least two diaphragm plates.

5. An x-ray diagnostic system as claimed in claim 3, wherein said diaphragm means is an iris diaphragm having a plurality of diaphragm plates all of which are synchronously moveable relative to each other and to said central ray.

6. An x-ray diagnostic system as claimed in claim 1, wherein said means for generating a mark is a means for generating a line mark.

7. An x-ray diagnostic system as claimed in claim 1, wherein each of said plurality of diaphragm plates has a radiation-limiting edge closest to said central ray, and wherein said means for generating a mark is a means for generating a mark having a contour corresponding to the shape of said radiation-limiting edge.

8. An x-ray diagnostic system as claimed in claim 1, wherein said means for generating said signal is directly connected to at least one of said diaphragm plates in said diaphragm means.

9. An x-ray diagnostic system as claimed in claim 1, wherein said diaphragm means includes at least one motor for moving said diaphragm plates, and wherein said means for generating said signal is connected to said motor.

10. An x-ray diagnostic system as claimed in claim 1, wherein said means for generating said signal is a stepping motor connected to said diaphragm means for moving said diaphragm plates in said diaphragm means.

11. A method for operating an x-ray diagnostics system for examining a patient comprising the steps of:

generating a transillumination image of said patient using an x-ray beam having a central ray;

storing said transillumination image;

gating said x-ray beam by moving a plurality of diaphragm plates into the path of said x-ray beam relative to said central ray;

generating a signal corresponding to the position of a diaphragm plate in said plurality of diaphragm plates relative to said central ray;

displaying the stored transillumination image;

generating a mark from said signal identifying the position of said diaphragm plate relative to said central ray; and mixing said mark into said stored transillumination image at a location in said stored transillumination image corresponding to the position of said diaphragm plate for simultaneous display with said stored transillumination image.

12. A method as claimed in claim 11, wherein the step of gating said x-ray beam is further defined by gating said x-ray beam with pairs of diaphragm plates, the plates in each pair of diaphragm plates being disposed on opposite sides of said central ray and being synchronously moveable relative to each other, wherein the step of generating a signal is further defined by generating a signal corresponding to the position of one diaphragm plate in each of said pair of diaphragm plates, and wherein the step of generating a mark is further defined by generating two marks respectively corresponding to the positions of each of the diaphragm plates in a pair of plates from the signal corresponding to the position of said one of said diaphragm plates.

13. A method as claimed in claim 11, wherein the step of gating said x-ray beam is further defined by gating said x-ray beam with a plurality of diaphragm plates all synchronously moveable relative to each other and to said central ray, wherein the step of generating said signal is further defined by generating a signal corresponding to the position of one of said diaphragm plates, and wherein the step of generating a mark is further defined by generating a plurality of marks respectively corresponding to the positions of each of said diaphragm plates from said signal corresponding to the position of said one of said diaphragm plates.

* * * * *